United States Patent [19]

Farrell

[11] Patent Number: 4,690,895

[45] Date of Patent: Sep. 1, 1987

[54] USE OF RLDM ™ 1-6 AND OTHER LIGNINOLYTIC ENZYMES IN THE BLEACHING OF KRAFT PULP

[75] Inventor: Roberta L. Farrell, Danvers, Mass.

[73] Assignee: Repligen Corporation, Cambridge, Mass.

[21] Appl. No.: 845,654

[22] Filed: Mar. 28, 1986

Related U.S. Application Data

[63] Continuation-in-part of Ser. No. 755,243, Jul. 15, 1985, abandoned.

[51] Int. Cl.⁴ .................. D21C 3/00; D21C 3/20; C12R 1/645
[52] U.S. Cl. ...................................... 435/278; 162/72
[58] Field of Search .................. 162/72; 435/189, 195, 435/196, 278

[56] References Cited

PUBLICATIONS

Alberti, B. N. and Klibanov, A. M. (1981) "Enzymatic Removal of Dissolved Aromatics from Industrial Aqueous Effluents" Biotechnology and Bioengineering Symp. 11:373–379.

Kirk, T. K. and Chang, H-M., (1981) "Potential Applications of Bio-Ligninolytic Systems" Enzyme Microb. Technol. 3:189–196.

Primary Examiner—Lionel M. Shapiro
Attorney, Agent, or Firm—Roman Saliwanchik; David R. Saliwanchik

[57] ABSTRACT

The subject invention concerns a novel enzymatic process for bleaching kraft pulp. Specifically, novel enzymes, designated rLDM ™, and other ligninolytic enzymes present in the extracellular growth medium from a fermentation of *Phanerochaete chrysosporium*, are used to bleach kraft pulp to a desired lighter color.

19 Claims, No Drawings

4,690,895

USE OF RLDM ™ 1-6 AND OTHER LIGNINOLYTIC ENZYMES IN THE BLEACHING OF KRAFT PULP

CROSS REFERENCE TO A RELATED APPLICATION

This is a continuation-in-part of my copending application Ser. No. 755,243, filed on July 15, 1985, now abandoned.

BACKGROUND OF THE INVENTION

The primary chemical method for making pulp from wood involves the digestion of lignin in the wood with sodium sulfide and sodium hydroxide. This is termed the sulfate or kraft process.

Wood pulp produced in the kraft process generally contains 5–8% by weight of residual, modified lignin which gives the pulp a characteristic brown color. To obtain a pulp of very high brightness and brightness stability, the lignin must be removed by certain oxidizing agents commonly referred to as bleaching chemicals. Many bleaching processes exist but almost all begin with the chlorinatior extraction (C-E) stage. There is a loss of cellulosic fibers during the C-E stage. The C-E effluents resulting from treated pulp contain a very large number of organic compounds having a bound chlorine content of 2.5–3.5 kg/ton pulp. Some of these compounds, primarily the chlorinated phenolics, are known to have toxic, mutagenic and carcinogenic effects. (Alberti, B.N. and Klibanov, A.M. [1981] Biotechnology and Bioengineering Symp. 11:373–379). These effluents are highly unsuited for recycling within the pulping system due to their high level of corrosive chlorides. Alternatives to chlorine bleaching have, therefore, long been sought by industry.

Hydrogen peroxide has been shown to deligninify sulfite pulps satisfactorily, but on its own it is a relatively ineffective means of bleaching kraft pulp. When used in sequences with chlorine-containing bleaching agents, however, peroxide contributes significantly to deligninification, pulp brightness and brightness stability.

Oxygen and ozone have been extensively studied for incorporation into the bleaching processes. The major disadvantage of these compounds is their non-specific oxidative attack on cellulosic fibers. Lower pulp yields tend to result and the pulp properties are generally inferior to those obtained with chlorine bleaching sequencing.

Research sponsored by the U.S. Department of Agriculture's (USDA) Forest Products Laboratory has demonstrated that 50–75% of the residual lignin was removed by fungal cultures of *Phanerochaete chrysosporium* in 6 to 8 days. Longer incubation resulted in greater lignin reductions, but the data were not quantified. During incubation, the pulp became substantially lighter in color. Furthermore, fungal deligninification of kraft pulps resulted in a concomitant reduction in the amount of chlorine required to produce a given level of brightness (Kirk, T. K. and Chang, H. [1981] Enzyme Microb. Technol. 3:189–196).

Bleaching is impractically slow using whole fungal cultures. It was found that lignin removal (i.e., kappa number decrease) from kraft pulp followed a triphasic pattern: 1) no lignin removal during establishment the fungus in the pulp over the first two days, 2) rapid deligninification during the following two days, and 3) slower deligninification thereafter. The initial two-day lag is due to the secondary metabolic importance of lignin degradation to fungal growth.

Another disadvantage of fungal bleaching is that these organisms contain enzymes which degrade both cellulose and hemicellulose. In any effective bleaching scheme, the degradation of cellulosic fibers must be completely suppressed, since the cellulosic fibers are particularly vulnerable after kraft pulping. Cellulase-less mutants have to some extent overcome this problem, but they are difficult to manage and are even less efficient in degrading lignin than normal fungal cultures. A final disadvantage of using fungal cells is that they can only operate optimally in an environment where temperature and microbial contamination are carefully controlled.

BRIEF SUMMARY OF THE INVENTION

The subject invention concerns the bleaching of kraft pulp with rLDM ™ and other ligninolytic enzymes. rLDM ™ are ligninases which are highly specific and which will degrade the hard-to-remove residual lignin polymers in chemical pulps without damaging cellulosic fibers.

rLDM ™ can bleach kraft pulp and they are immediately active. Thus, there is no lag in activity as with fungal cultures. Since the rLDM ™ are biological molecules, they are, advantageously, not corrosive, do not cause pollution, and do not present an environmental hazard when released.

The lignin-degrading enzymes of the invention, referred to as rLDM ™, are referred to as Pulpases ™ in co-pending application Ser. No.755,243.

DETAILED DESCRIPTION OF THE INVENTION

The rLDM ™ which can be used in the subject invention process were isolated from a novel stable mutant strain of the white-rot fungus *Phanerochaete chrysosporium*. The novel mutant strain, designated SC26, has been deposited in the permanent collection of a public culture repository, to be maintained for at least 30 years. The culture repository is the Northern Regional Research Laboratory, U.S. Department of Agriculture, Peoria, Illinois 61604, USA. The accession number is NRRL 15978, and the deposit date is July 3, 1985. This deposited culture is available to the public upon the grant of a patent disclosing it. The deposit also is available as required by foreign patent laws in countries wherein counterparts of the subject application, or its progeny, are filed. However, it should be understood that the availability of a deposit does not constitute a license to practice the subject invention in derogation of patent rights granted by governmental action.

Novel mutant SC26 was obtained by UV mutagenesis of the wild type *Phanerochaete chrysosporium*, ATCC 24725.

Novel mutant SC26 was grown on a nitrogen-limited trace element medium supplemented with glucose and buffered at pH 4.5.

Isolation and purification of the ligninases from the extracellular fluid in the fermentation was accomplished by ultrafiltration and fast protein liquid chromatography (FPLC) using an anion exchange column.

The rLDM ™ used in the subject invention process were prepared as follows:

PREPARATIVE

Example 1—Growth of Mutant SC26 (NRRL 15978) to Produce Fermentation Medium Containing Novel Ligninases Inoculum was prepared by homogenizing 50 ml of 1.5-day cultures of mutant SC26 grown in 1 liter flasks containing the following medium, designated nitrogen-limited BIII/glucose medium:

The BIII medium contains $1.08 \times 10^{-3}$ M ammonium tartrate, $1.47 \times 10^{-2}$ M $KH_2PO_4$, $2.03 \times 10^{-3}$ M $MgSO_4 \cdot 7H_2O$, $6.8 \times 10^{-4}$ M $CaCl_2O$, $2.96 \times 10^{-6}$ M thiamine.HCl and 10 ml.$L^{-1}$ of a trace element solution. The trace element solution contains $7.8 \times 10^{-3}$ M nitriloacetic acid, $1.2 \times 10^{-2}$ M $MgSO_4 \cdot 7H_2O$, $1.7 \times 10^{-2}$ M NaCl, $3.59 \times 10^{-4}$ M $FeSO_4.7H_2O$, $7.75 \times 10^{-4}$ M $CoCl_2$, $9.0 \times 10^{-4}$ M $CaCl_2$, $3.48 \times 10^{-4}$ M $ZnSO_4 \cdot 7H_2O$, $4 \times 10^{-5}$ M $CuSO_4 \cdot 5H_2O$, $2.1 \times 10^{-5}$ M $AlK(SO_4)_2 \cdot 12H_2O$, $1.6 \times 10^{-4}$ M $H_3BO_3$, $4.1 \times 10^{-5}$ M $NaMoO_4 \cdot 2H_2O$ and $2.9 \times 10^{-3}$ M $MnSO_4.H_2O$.

The medium was supplemented with 10% (by wt/liter) of glucose.

The medium was buffered with 10 mM trans-aconitic acid, pH 4 5.

Flasks (125 ml, containing 10 ml sterile medium having the above-described medium) were each inoculated with 0.5 ml of the above homogenate and kept stationary at 39° C. The flasks were flushed on days 0, 3, and 6 with water-saturated $O_2$. Alternatively, a rotating biological contractor (RBC) was used to grow the fungus. 2.5 liters of the above-described medium was inoculated with 100 ml of the above homogenate and grown at 39° C. with the RBC rotating at 1 rpm with continuous oxygenation.

Ligninase activity was measured periodically by determining the rate of oxidation of veratryl alcohol to veratrylaldehyde. Reaction mixtures contained 275 $\mu$l of extracellular fluid (from flasks or the RBC), 2 mM veratryl alcohol, 0.4 mM $H_2O_2$ and 0.1 mM sodium tartrate, pH 2.5. in a final volume of 0.5 ml. The reactions were started by $H_2O_2$ addition immediately after buffer was added and were monitored at 310 nm. Protein was determined according to Bradford (Bradford, M.M. [1976]Anal. Biochem. 72:248-254) using bovine serum albumin (Sigma Chemical, St. Louis, MO) as standard.

PREPARATIVE

Example 2—Isolation and Purification of the Novel rLDM TM

The extracellular growth media from cultures grown in flasks, as described above, was harvested by centrifugation at $5000 \times G$, 10 min, 4° C. Extracellular growth media was then concentrated by ultrafiltration through a 10K. filter. The resulting concentrate is called the Ligninolytic Mixture TM. The rLDM TM contained in this Ligninolytic Mixture TM were separated by fast protein liquid chromatography (FPLC) using a Pharmacia Mono Q column (Pharmacia, Piscataway, NJ) and a gradient of sodium acetate buffer, pH 6, from 10 mM to 1 M. rLDM TM 1, 2, 3, 4, 5, and 6 elute from the column in a typical preparation at the following sodium acetate molarities, respectively: 0.16, 0.18, 0.34, 0.40, 0.58, and 0.43 M to give essentially pure rLDM TM 1-6. Each rLDM TM is substantially free of other rLDM TM and native proteins.

Characterization of the Novel rLDM TM

The rLDM TM have been characterized by the following criteria:

(1) ability to catalyze the oxidation of veratryl alcohol to veratrylaldehyde;
(2) molecular weight as determined by SDS-PAGE;
(3) amino acid composition;
(4) heme content;
(5) homology by antibody reactivity
(6) specificity of activity against lignin model substrates: and
(7) elution from an FPLC column at specified sodium acetate molarities.

All of the rLDM TM catalyze the oxidation of veratryl alcohol to veratrylaldehyde, as monitored spectrophotometrically at 310 nm. A unit of activity is defined as the production of 1 micromole of veratrylaldehyde in the rLDM TM catalyzed reaction. The specific activities of typical preparations at about 24° C. are as follows:

| rLDM TM | 1 | 2 | 3 | 4 | 5 | 6 |
|---|---|---|---|---|---|---|
| SPECIFIC ACTIVITY UNITS/MG · MINUTE | 2.6 | 17.1 | 5.1 | 9.7 | 9.4 | 12.4 |
| MOLECULAR WEIGHT kD | 38 | 38 | 42 | 42 | 43 | 42 |

Amino acid composition—See Table 1.

Heme and carbohydrate content—rLDM TM 1, 2, 3, 4, 5, and 6 each contain a single protoheme IX Moiety. All are glycosylated according to periodic acid staining (PAS) and binding to Con A-Sepharose (Sigma).

TABLE I

| Amino Acid | Amino Acid Composition of rLDM TM | | | | |
|---|---|---|---|---|---|
|  | rLDM TM 1 Ratio | rLDM TM 2 Ratio | rLDM TM 3 Ratio | rLDM TM 5 Ratio | rLDM TM 6 Ratio |
| asp/asn | 1.4 | 2.0 | 5.4 | 5.0 | 3.0 |
| glu/gln | 6.0 | 7.7 | 16.8 | 19.9 | 8.0 |
| ser | 4.3 | 4.1 | 14.0 | 22.3 | 6.8 |
| his | 4.4 | 3.2 | 7.3 | 15.9 | 3.2 |
| gly | 6.5 | 5.7 | 24.0 | 44.7 | 8.3 |
| thr | 2.2 | 3.5 | — | — | 4.9 |
| arg | 1.1 | 1.2 | 2.9 | 4.8 | 1.3 |
| ala | 7.3 | 7.9 | 14.4 | 13.8 | 6.7 |
| tyr | 0.2 | — | 1.0 | 1.0 | 0.2 |
| met | — | — | 1.2 | — | 0.14 |
| val | 1.6 | 2.6 | 7.4 | 6.5 | 4.2 |
| phe | 1.1 | 3.0 | 7.0 | 3.3 | 3.2 |

TABLE I-continued

| Amino Acid | Amino Acid Composition of rLDM ™ | | | | |
|---|---|---|---|---|---|
| | rLDM ™ 1 Ratio | rLDM ™ 2 Ratio | rLDM ™ 3 Ratio | rLDM ™ 5 Ratio | rLDM ™ 6 Ratio |
| ile | 1.0 | 2.2 | 4.1 | 3.6 | 2.4 |
| leu | 1.5 | 2.6 | 6.5 | 6.0 | 3.3 |
| lys | 0.5 | 1.0 | 2.5 | 2.3 | 1.0 |

IMMUNOBLOT PROCEDURE

This procedure was used to further characterize the rLDM ™. It is a standard procedure which is disclosed in Towbin et al. (Towbin, H., Staehelin, T. and Gordon, J. [1979]Proc. Natl. Acad. Sci. USA 76:4350). The procedure involves separating the proteins by electrophoresis in a gel, transfer of the proteins to a solid matrix, and reacting with (1) a primary probe, rabbit anti-rLDM ™ antibody and (2) a secondary probe, goat anti-rabbit antibody coupled to horseradish peroxidase.

rLDM ™ 1, 3, 4, 5, and 6 react to polyclonal antibodies made to rLDM ™ 2 and 6, using the above immunoblot procedure rLDM ™ 2, in the same procedure, reacts to polyclonal antibodies made to rLDM ™ 6.

All the rLDMυ disclosed herein have the following unique activities on lignin model substrates:
(1) oxidative cleavage of $C_A-C_\beta$;
(2) hydroxylation of benzylic methylene groups;
(3) oxidation of benzyl alcohols to aldehydes;
(4) phenol oxidation and
(5) oxidation of methoxy and ethoxy benzene.

"Lignin model substrates" are chemicals which resemble parts of lignin. The above activities are characteristic of the rLDM ™ disclosed herein.

Following are Examples which illustrate the best mode for practicing the invention. These Examples should not be construed as limiting. In all Examples herein, percentages are by weight and solvent mixture proportions are by volume unless otherwise noted.

Example 1—Bleaching of Kraft Pulp with rLDM ™ and Other Ligninolytic Enzymes The Ligninolytic Mixture ™, as described in Preparative Example 2, was added to kraft pulp having a characteristic brown color at 3% consistency in 10 mM trans-aconitic acid, pH 4.5, 400 μM $H_2O_2$ and 100 μM $MnSO_4$. The pulp slurry was flushed with $O_2$ and incubated with slow shaking at 39° C. for 12 hr, after which the kraft pulp solution was decanted, and a 1 M NaOH solution was added to the pulp and incubated for 60 min at 65° C. This was then decanted and the kraft pulp was washed in water. The resulting kraft pulp no longer had a dark brown color, but instead had a desired lighter color.

The use of $MnSO_4$ is optional. Regarding the above conditions, for each of the parameters there is a range of values which can be used to achieve the desired result. Typical values and acceptable ranges for each parameter are shown in Table 2.

EXAMPLE 2 rLDM ™ 1 through 6, individually, or mixtures thereof, can be used to treat kraft pulp using essentially the same procedures as disclosed in Example 1, including ranges, or obvious modifications thereof. The resulting kraft pulp is of the desired lighter color.

EXAMPLE 3

Upon substituting the Ligninolytic Mixture ™ of Example 1 with extracellular growth medium, prepared as disclosed in Preparative Example 1, there is obtained kraft pulp having a desired lighter brown color.

EXAMPLE 4

Upon substituting the Ligninolytic Mixture1υ of Example 1 with a mixture comprising all of the following or any combination thereof: rLDM ™ 1-6, individually or mixtures thereof: Ligninolytic Mixture ™ and extracellular growth medium: there is obtained kraft pulp having a desired lighter brown color.

The rLDM ™ of the subject invention can be used in the crude form, in a purified form, wherein each rLDM ™ is substantially free of other rLDM ™ and native proteins, and in mixtures thereof. It is well within the skill of a person skilled in the art to adjust amounts of rLDM ™ used in accordance with the purity of the rLDM ™ preparation.

"Native proteins" as used herein refers to other proteins present in the extracellular fermentation medium, as described above.

TABLE 2

| Parameter | Typical | Range |
|---|---|---|
| Consistency | 3% | 0.01 to 20%* |
| Concentration of trans-aconitic acid** | 10 mM | 0.005 to 0.5 M |
| pH | 4.5 | 2 to 7 |
| Concentration of $H_2O_2$ | 400 μM | 2 μM to 10 mM |
| Concentration of $MnSO_4$ | 100 μM | 10 to 500 μM |
| Incubation of pulp slurry (First incubation) | 12 hr | 2 min to 48 hr |
| Temperature of first incubation | 39° C. | 15° to 50° C. |
| Concentration of NaOH*** | 1 M | 0.01 to 5 M |
| Incubation of pulp after alkaline treatment (Second incubation) | 60 min | 2 min to 48 hr |
| Temperature of second incubation | 65° C. | 5° to 100° C. |

*Concentrations greater than 20% can be used if the fluid consistency of the medium is maintained.
**Other nontoxic enzyme buffers such as ammonium tartrate can be used.
***KOH or other alkaline solutions can be used.

We claim:
1. A process for bleaching kraft pulp which comprises treating said kraft pulp with extracellular growth medium from a fermentation of phanerochaete chrysosporium consisting essentially of rLDM ™ 1 through 6, and other ligninolytic enzymes.
2. A process, according to claim 1, wherein said *Phanerochaete chrysosporium* is the novel mutant strain designated SC26, having the identifying characteristics of NRRL 15978.
3. A process for bleaching kraft pulp which comprises treating said kraft pulp with Ligninolytic Mixture ™ from a fermentation of Phanerochaete chrysosporium consisting essentially of rLDM ™ 1 through 6, and other ligninolytic enzymes.

4. A process, according to claim 3, wherein said *Phanerochaete chrysosporium* is the novel mutant strain designated SC26, having the identifying characteristics of NRRL 15978.

5. A process for bleaching kraft pulp which comprises treating said kraft pulp with an rLDM ™ selected from the group consisting of rLDM ™ 1, rLDM ™ 2, rLDM ™ 3, rLDM ™ 4, rLDM ™ 5, and rLDM ™ 6, or mixtures thereof.

6. A process for bleaching kraft pulp which comprises treating said kraft pulp with a mixture comprising one or more of the following rLDM ™ 1 through 6, individually or a mixture thereof; Ligninolytic Mixture ™ from a fermentation of Phanerochaete chrysosporium comprising RLDM ™ 1 through 6, and other ligninolytic enzymes; and extracellular growth medium from a fermentation of Phanerochaete chrysosporium consisting essentially of RLKM ™ 1 through 6, and other ligninolytic enzymes.

7. A process, according to claim 6, wherein said *Phanerochaete chrysosporium* is the novel mutant strain designated SC26, having the identifying characteristics of NRRL 15978.

8. A process, according to claim 1, wherein the extracellular growth medium from a fermentation of *Phanerochaete chrysosporium is added to kraft pulp which is in about 2 µM to about 10 mM $H_2O_2$, buffered at about pH 2 to about pH 7 and has a consistency of about 0.01% to about 20%; the resulting pulp slurry is then shaken at about 15° C. about 50° C. for about 2 min to about 48 hr; decanted; about 0.01 to about 5 M of an alkaline solution is added; the resulting slurry is incubated at about 5° C. to about 100° C. for about 2 min to about 48 hr; decanted; and washed in water to obtain bleached kraft pulp.

9. A process, according to claim 3 wherein the Ligninolytic Mixture ™ from a fermentation of Phanerochaete chrysosporium* is added to kraft pulp which is in about 2 µm to about 10 mM $H_2O_2$, buffered at about pH 2 to about pH 7 and has a consistency of about 0.01% to about 20%; the resulting pulp slurry is then shaken at about 15° C. to about 50° C. for about 2 min to about 48 hr; decanted; about 0.01 to about 5 M of an alkaline solution is added; the resulting slurry is incubated at about 5° C. to about 100° C. for about 2 min about 48 hr; decanted; and washed in water to obtain bleached kraft pulp.

10. A process, according to claim 3, wherein the Ligninolytic Mixture ™ from a fermentation of *Phanerochaete chyrysosporium* is added to kraft pulp which is in 400 µM $H_2O_2$, buffered at about pH 4.5, and has a consistency of about 3%; the resulting pulp slurry is then shaken at about 39° C. for about 12 hr; decanted; about 1 M NaOH is added; the slurry is incubated at about 65° C. for 60 min; decanted; and washed in water to obtain bleached kraft pulp.

11. A process, according to claim 1, wherein about 10 to about 500 µM $MnSO_4$ is added with the extracellular growth medium.

12. A process, according to claim 2, wherein about 10 to about 500 µM $MnSO_4$ is added with the extracellular growth medium.

13. A process, according to claim 3, wherein about 10 to about 500 µM $MnSO_4$ is added with the Ligninolytic Mixture ™ .

14. A process, according to claim 4, wherein about 10 to about 500 µM $MnSO_4$ is added with the Ligninolytic Mixture ™ .

15. A process, according to claim 13, wherein the concentration of $MnSO_4$ is about 100 µM.

16. A process, according to claim 14, wherein the concentration of $MnSO_4$ is about 100 µM.

17. A process, according to claim 8, wherein said *Phanerochaete chrysosporium* is the novel mutant strain SC26, having the identifying characteristics of NRRL 15978.

18. A process, according to claim 9, wherein said *Phanerochaete chrysosporium* is the novel mutant strain SC26, having the identifying characteristics of NRRL 15978.

19. A process, according to claim 10, wherein said *Phanerochaete chrysosporium* is the novel mutant strain SC26, having the identifying characteristics of NRRL 15978.

* * * * *

UNITED STATES PATENT AND TRADEMARK OFFICE
CERTIFICATE OF CORRECTION

PATENT NO. : 4,690,895                                      Page 1 of 2

DATED : September 1, 1987

INVENTOR(S) : Roberta L. Farrell

It is certified that error appears in the above-identified patent and that said Letters Patent are hereby corrected as shown below:

On The Title Page,

In the title, "RLDM$^{TM}$" should read --rLDM$^{TM}$--

Col. 1: line 1: "RLDM$^{TM}$" should read --rLDM$^{TM}$--; line 24: "chlorinatior" should read --chlorination--; line 66: "establishment" should read --establishment of--.

Col. 3: line 12: "CaCl$_2$O" should read --CaCl$_2$· 2H$_2$O--; line 41: "2.5." should read --2.5--.

Col. 4: line 24: "reactivity" should read --reactivity;--; line 26: "strates:" should read --strates;--.

Col. 5: line 24: "procedure" should read --procedure.--; line 27: "rDLM↵" should read --rDLM$^{TM}$--; line 29: "C$_\Delta$" should read --C$_f$--.

Col. 6: line 18: "Mixture1↵" should read --Mixture$^{TM}$--; line 21: "thereof:" should read --thereof;--; "Mixture$^{TM}$" should read --Mixture$^{TM}$;--; line 22: "medium:" should read --medium;--; line 57: "phanerochaete" should read --Phanerochaete--; italicize "Phanerochaete chrysosporium"; line 66 & 67: italicize "Phanerochaete chrysosporium".

UNITED STATES PATENT AND TRADEMARK OFFICE
CERTIFICATE OF CORRECTION

PATENT NO. : 4,690,895

DATED : September 1, 1987

INVENTOR(S) : Roberta L. Farrell

It is certified that error appears in the above-identified patent and that said Letters Patent are hereby corrected as shown below:

Col. 7: lines 14 & 15: <u>Italicize</u> "Phanerochaete chrysosporium"; line 15: "RLDM$^{TM}$" should read-- rLDM$^{TM}$--; line 17: <u>italicize</u> "Phanerochaete chrysosporium"; line 18: "RLKM$^{TM}$" should read-- rLDMT$^M$--; line 26 & 27: "is added to kraft pulp which is in about" <u>should not be italicized</u>; line 30: "15°C" should read --15°C to--; line 36: "3" should read --3,--; line 39: " m" should read -- M--.

Col. 8: line 2: "min" should read "min to".

Signed and Sealed this

Second Day of February, 1988

Attest:

DONALD J. QUIGG

Attesting Officer

Commissioner of Patents and Trademarks